(12) United States Patent
Lin et al.

(10) Patent No.: US 10,016,387 B2
(45) Date of Patent: *Jul. 10, 2018

(54) METHOD FOR TREATING MELANOMA

(71) Applicant: TCI CO., LTD, Taipei (TW)

(72) Inventors: Yung-Hsiang Lin, Taipei (TW); Jui-Ying Cho, Taipei (TW)

(73) Assignee: TCI CO., LTD., Taipei (TW)

( * ) Notice: Subject to any disclaimer, the term of this patent is extended or adjusted under 35 U.S.C. 154(b) by 0 days.

This patent is subject to a terminal disclaimer.

(21) Appl. No.: 15/710,395

(22) Filed: Sep. 20, 2017

(65) Prior Publication Data

US 2018/0085340 A1    Mar. 29, 2018

Related U.S. Application Data

(60) Provisional application No. 62/398,675, filed on Sep. 23, 2016.

(51) Int. Cl.
    *A61K 31/34*      (2006.01)

(52) U.S. Cl.
    CPC .................................. *A61K 31/34* (2013.01)

(58) Field of Classification Search
    None
    See application file for complete search history.

(56) References Cited

U.S. PATENT DOCUMENTS

2002/0132021 A1*   9/2002   Raskin .................... A01H 3/00
                                                                                                                       424/773
2009/0004302 A1*   1/2009   Cyr ........................ A61K 36/15
                                                                                                                       424/732

OTHER PUBLICATIONS

CAS Accession No. 2012:1380836 (containing summary of Li et al (CN 102675270)) (Year: 2012).*
Machine Translation of Li et al (CN 102675270) (Year: 2012).*

* cited by examiner

*Primary Examiner* — Craig D Ricci
(74) *Attorney, Agent, or Firm* — Christensen, Fonder, Dardi & Herbert PLLC

(57) ABSTRACT

Method for treating melanoma is provided. The method comprises administering to a subject in need an effective amount of active ingredient, wherein the active ingredient is selected from the following group: a compound of formula (I), a pharmaceutically acceptable salt of the compound of formula (I), and combinations thereof,

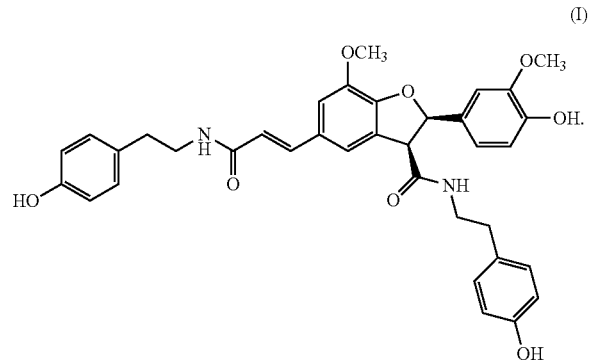

9 Claims, 1 Drawing Sheet

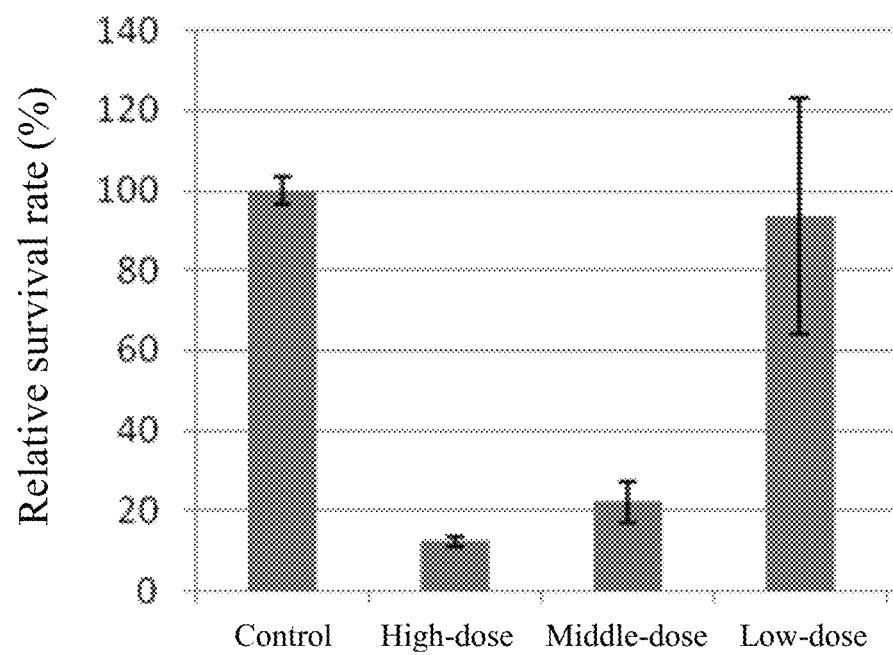

METHOD FOR TREATING MELANOMA

FIELD OF THE INVENTION

The present invention relates to the uses of a compound of formula (I), a pharmaceutically acceptable salt of the compound of formula (I), and combinations thereof, and especially relates to the uses of a compound of formula (I), a pharmaceutically acceptable salt of the compound of formula (I), and combinations thereof in treating melanoma:

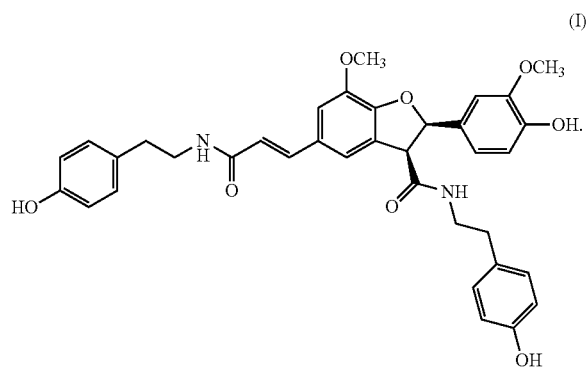 [SMILES: COc1cc([C@@H]2Oc3c(OC)cc(/C=C/C(=O)NCCc4ccc(O)cc4)cc3[C@@H]2C(=O)NCCc2ccc(O)cc2)ccc1O]

(I)

BACKGROUND OF THE INVENTION

Melanoma, a cancer that develops from melanocytes, easily metastasizes and spreads though the lymphatic system or blood, making it difficult to treat, and thus, is the most lethal form of skin cancer. Exposure to ultraviolet light is the principle cause of melanoma. Other factors such as family inheritance and hypo-immunity may also cause melanoma. Currently, the primary method for treating melanoma clinically is surgical resection. For the treatment of patients whose tumor cannot be resected completely or for patients who cannot afford surgery, immunotherapy and chemotherapy are generally used instead. However, immunotherapy and chemotherapy are expensive and have severe side effects (including emesis, alopecia, fatigue, hemorrhaging and anemia), and are not effective for some patients in the late stage of melanoma. Therefore, there is a necessity and urgency to develop a drug or a method for treating melanoma effectively.

Inventors of the present invention found that N-trans-grossaminde (i.e., the compound of formula (I) of the present invention) is effective in inducing apoptosis of malignant melanoma cells, and thus, can be used for treating melanoma.

SUMMARY OF THE INVENTION

An objective of the present invention is to provide a use of an active ingredient in the manufacture of a medicament used for treating melanoma, wherein the active ingredient is selected from the group consisting of a compound of formula (I), a pharmaceutically acceptable salt of the compound of formula (I), and combinations thereof,

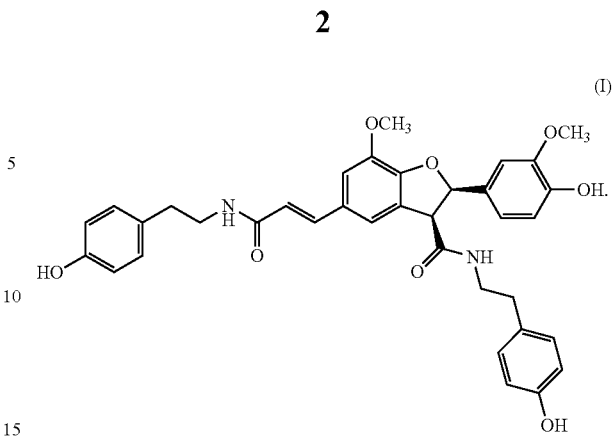

(I)

In a preferred embodiment of the use in accordance with the present invention, the active ingredient is provided as an extract. More preferably, the active ingredient is provided as an extract of *Mesembryanthemum crystallinum* L. Even more preferably, the active ingredient is provided as a polar solvent extract of *Mesembryanthemum crystallinum* L., wherein the polar solvent is selected from the group consisting of water, C1-C4 alcohols, and combinations thereof.

Preferably, the medicament is administered by at least one of oral administration, percutaneous administration and injection.

Another objective of the present invention is to provide a method for treating melanoma, comprising administering to a subject in need an effective amount of an active ingredient, wherein the active ingredient is selected from the group consisting of a compound of formula (I), a pharmaceutically acceptable salt of the compound of formula (I), and combinations thereof,

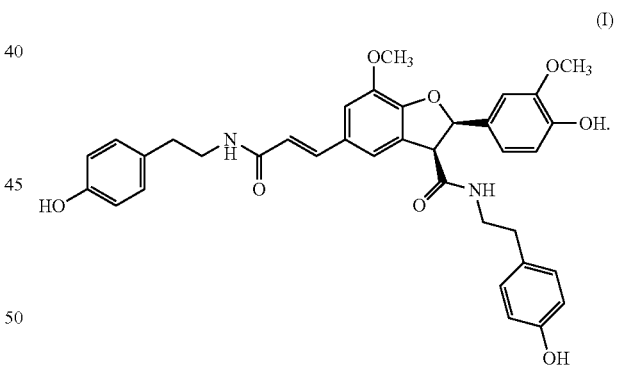

(I)

The detailed technology and preferred embodiments implemented for the present invention are described in the following paragraphs for people skilled in this field to well appreciate the features of the claimed inventive.

BRIEF DESCRIPTION OF THE DRAWINGS

FIG. 1 is a bar diagram showing the survival rates of *homo sapiens* skin malignant melanoma cells (A375.S2 cell line) in the control group, high-dose group, middle-dose group and low-dose group, wherein the cells of different groups have been treated with different doses of the compound of formula (I) of the present invention.

DESCRIPTION OF THE PREFERRED EMBODIMENTS

The following will describe some embodiments of the present invention in detail. However, without departing from the spirit of this invention, the present invention may be embodied in various embodiments and should not be illustrated as limited to the embodiments descried in the specification. In addition, unless otherwise indicated herein, the expressions "a," "an," "the," or the like recited in this specification (especially in the claims) are intended to include both the singular and plural forms. The term "an effective amount" recited in this specification refers to the amount of a compound that can at least partially alleviate the condition of a suspected subject. The term "subject" recited in this specification refers to a mammalian, including human and non-human animals. Furthermore, the term "treat" or "treating" recited in the specification should not be construed as treating a subject until the subject is completely recovered, but should include maintaining the progression or symptoms of the diseases in a substantially static state, increasing the recovery rate of a subject, alleviating the severity of a particular condition of illness, and increasing the quality of life for a patient.

*Mesembryanthemum crystallinum* L. is an annual dicotyledonous plant, which belongs to the Aizoaceae family, *Mesembryanthemum* genus. Inventors of the present invention found that the extract of *Mesembryanthemum crystallinum* L. contains a compound of formula (I) as shown below. The compound of formula (I) is effective in inducing apoptosis of *homo sapiens* skin malignant melanoma cells, and thus, can be used for treating melanoma:

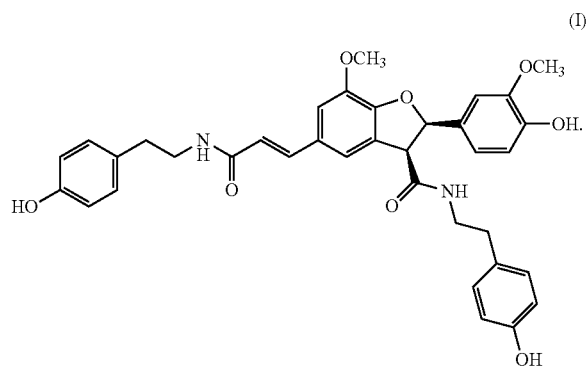 [SMILES: COc1cc([C@@H]2Oc3c(OC)cc(/C=C/C(=O)NCCc4ccc(O)cc4)cc3[C@@H]2C(=O)NCCc2ccc(O)cc2)ccc1O]

(I)

Therefore, the present invention provides the medicaments and methods for treating melanoma, wherein the medicament comprises an active ingredient, and the method comprises administering an effective amount of an active ingredient to a subject in need. In the medicaments and methods in accordance with the present invention, the active ingredient is selected from the group consisting of a compound of formula (I) as described above, a pharmaceutically acceptable salt of the compound of formula (I), and combinations thereof.

The compound of formula (I) in accordance with the present invention can be provided from any suitable source. For example, the compound of formula (I) can be purchased commercially, be purified and isolated from a plant extract, or be obtained by a chemical synthesis method. For example, the compound of formula (I) can be extracted and purified from *Mesembryanthemum crystallinum* L.

According to the present invention, the active ingredient can also be provided as a mixture of plant extracts. For example, the plant extract can be an extract of *Mesembryanthemum crystallinum* L.; and preferably, the plant extract is a polar solvent extract of *Mesembryanthemum crystallinum* L. When the active ingredient required by the present invention is provided as a polar solvent extract of *Mesembryanthemum crystallinum* L., the adopted polar solvent can be, for example, water, C1-C4 alcohols or combinations thereof. For example, an aqueous ethanol solution can be used for extracting *Mesembryanthemum crystallinum* L. to provide the desired extract. Optionally, the extraction can be performed with an ultrasonic oscillation to increase the extraction efficiency. Preferably, the plant (such as *Mesembryanthemum crystallinum* L.) is subject to a drying treatment prior to the extraction.

Depending on the desired administration manner, the medicament in accordance with the present invention can be provided in any suitable form without particular limitations. For example, the medicament can be administered to a subject in need via an oral or parenteral (such as subcutaneous, intravenous, or percutaneous) route to treat melanoma, but is not limited thereby.

As a dosage form suitable for percutaneous administration, the medicament can be provided in a form of an emulsion, a cream, a gel (such as a hydrogel), a paste (such as a dispersing paste, an ointment), a spray, or a solution (such as a lotion, a suspension) for external use, but is not limited thereby. Depending on the form and purpose, suitable carriers can be chosen and used to provide the medicament, wherein the carriers include excipients, diluents, auxiliaries, stabilizers, absorbent retarders, disintegrants, hydrotropic agents, emulsifiers, antioxidants, adhesives, binders, tackifiers, dispersants, suspending agents, lubricants and/or hygroscopic agents.

As a dosage form suitable for oral administration, the medicament may comprise any pharmaceutically acceptable carrier that will not adversely affect the desired effects of the active ingredient of the present invention (i.e., compound of formula (I), pharmaceutically acceptable salt of the compound of formula (I), and combinations thereof). For example, the pharmaceutically acceptable carriers can be selected from a group consisting of water, saline, dextrose, glycerol, ethanol or its analogs, cellulose, starch, sugar bentonite, and combinations thereof. The medicament can be provided using any suitable manner to be made in any suitable form for oral administration, such as a tablet (e.g., dragee), a pill, a capsule, a granule, a pulvis, a fluidextract, a solution, syrup, a suspension, a tincture, etc.

As for the form of injection or drip suitable for subcutaneous or intravenous injection administration, the medicament may comprise one or more ingredient(s), such as an isotonic solution, a salt-buffered saline (e.g., phosphate-buffered saline or citrate-buffered saline), a hydrotropic agent, an emulsifier, 5% sugar solution, and other carriers to provide the medicament as an intravenous infusion, an emulsified intravenous infusion, a powder for injection, a suspension for injection, or a powder suspension for injection. Alternatively, the medicament may be prepared as a pre-injection solid. The pre-injection solid can be provided in a form which is soluble in other solutions or suspensions, or in an emulsifiable form. A desired injection is provided by dissolving the pre-injection solid in other solutions or suspensions or emulsifying it prior to being administered to a subject in need.

Optionally, the medicament provided in accordance with the present invention may further comprise a suitable amount of additives, such as a flavoring agent, a toner, or a coloring agent for enhancing the palatability and the visual perception of the medicament, and/or a buffer, a conservative, a preservative, an antibacterial agent, or an antifungal agent for improving the stability and storability of the medicament. In addition, the medicament may optionally further comprise one or more other active ingredient(s) (such as Zelboraf, Tafinlar and Yervoy), or be used in combination with a medicament comprising one or more other active ingredient(s), to further enhance the effects of the medicament or to increase the application flexibility and adaptability of the preparation thus provided, as long as the other active ingredients will not adversely affect the desired effects of the medicament of the present invention.

Depending on the desire, age, body weight, and health conditions of the subject, the medicament provided by the present invention may be administered at various dosing frequencies, such as once a day, multiple times a day, or once every few days.

In the method for treating melanoma in accordance with the present invention, the source, applied route, applied form, suitable dosage and use of the active ingredients (i.e., compound of formula (I), pharmaceutically acceptable salt of the compound of formula (I), and combinations thereof) are all in line with the above descriptions.

The present invention will be further illustrated in detail with specific examples as follows. However, the following examples are provided only for illustrating the present invention and the scope of the present invention is not limited thereby. The scope of the present invention will be indicated in the appended claims.

EXAMPLES

Sources of the materials used in the following Examples:
1. *Mesembryanthemum crystallinum* L. seeds: purchased from Taiwan Vegetable House-Horticultural Supplies, product number: 00K20.
2. *Homo sapiens* skin malignant melanoma cells (A375.S2 cell line): purchased from ATCC, product number: CRL-6475.
3. MEM-NEAA medium: purchased from Gibco, product number: 41500-034.
4. FBS: purchased from Gibco, product number: 10437-028.

Example 1

Preparation of Compound of Formula (I)

The *Mesembryanthemum crystallinum* L. seeds were cultivated into *Mesembryanthemum crystallinum* L. plants, and then the plants were treated by the following steps:
1. freeze-drying 20 g of the tissue sample of *Mesembryanthemum crystallinum* L. plants;
2. crushing the freeze-dried tissue sample of step 1 to provide a *Mesembryanthemum crystallinum* L. tissue powder;
3. mixing the *Mesembryanthemum crystallinum* L. tissue powder obtained from step 2 with 200 g of 70% ethanol solution to provide a mixture, and then ultrasonic oscillating the mixture at 70° C. for 30 minutes to obtain a crude extract;
4. vacuum-concentrating the crude extract obtained from step 3 to provide an ethanol extract (about 5.35 g);
5. adding ethyl acetate and water (v/v, ethyl acetate:water=1:1) into the ethanol extract obtained from step 4 to provide a mixed solution (the total volume was 200 ml), and subjecting the mixed solution to a liquid-liquid partition, thereafter, removing the water layer to obtain an ethyl acetate layer extract (about 2.29 g);
6. subjecting the ethyl acetate layer extract obtained from step 5 to an isolation by column chromatography (the silica gel used therein: 70 to 230 mesh, about 80 g), wherein the isolation was started with the use of dichloromethane as the elution solution, and the ratio of methanol in the elution solution was gradually increased to increase the polarity of the elution solution, so that the following four fractions were obtained sequentially:
   (i) first fraction (A1): 160 ml of mixed solution, wherein the volume ratio of dichloromethane:methanol=90:1;
   (ii) second fraction (A2): 160 ml of mixed solution, wherein the volume ratio of dichloromethane:methanol=80:1;
   (iii) third fraction (A3): 140 ml of mixed solution, wherein the volume ratio of dichloromethane:methanol=70:1; and
   (iv) forth fraction (A4): 200 ml of mixed solution, wherein the volume ratio of dichloromethane:methanol=50:1;
7. subjecting the forth fraction (A4) obtained from step 6 to an isolation by column chromatography (the silica gel used therein: 70 to 230 mesh, about 80 g), wherein the isolation was started with the use of a mixed solution of ethyl acetate and trichloromethane (v/v, ethyl acetate:trichloromethane=5:1) as the elution solution, so that ten sub-fractions (A4-1 to A4-10, 30 ml for each) were obtained sequentially; and
8. subjecting the A4-2 sub-fraction obtained from step 7 to a purification by preparative thin layer chromatography (the silica gel used therein: 70 to 230 mesh, about 80 g; and a mixed solution being prepared by mixing dichloromethane and acetone at a volume ratio of dichloromethane:acetone=2:1) to obtain compound of formula (I) as shown below (about 4.7 mg; Rf=0.55):

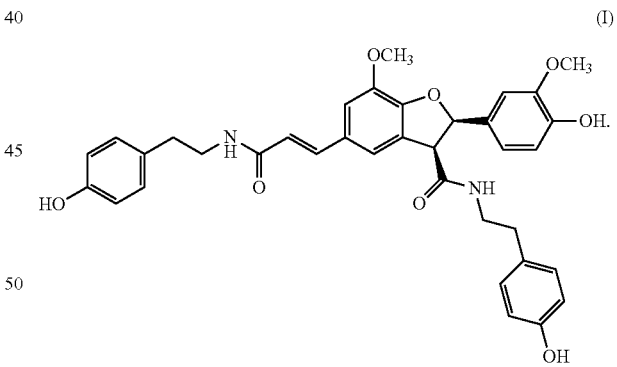

Example 2

Effects of Compound of Formula (I) on Treating Melanoma

*Homo sapiens* skin malignant melanoma cells (A375.S2 cell line) were cultivated for 24 hours, and then divided into four groups ($5 \times 10^3$ cells for each group). The four groups were respectively cultivated in the following medium for 48 hours:
1. Control group: a MEM-NEAA medium contains 1 mmol of sodium pyruvate and 10% of FBS.

2. High-dose group: a MEM-NEAA medium contains 1 mmol of sodium pyruvate, 10% of FBS and 1 mg/ml of the compound of formula (I) obtained from Example 1.
3. Middle-dose group: a MEM-NEAA medium contains 1 mmol of sodium pyruvate, 10% of FBS and 0.5 mg/ml of the compound of formula (I) obtained from Example 1.
4. Low-dose group: a MEM-NEAA medium contains 1 mmol of sodium pyruvate, 10% of FBS and 0.25 mg/ml of the compound of formula (I) obtained from Example 1.

Thereafter, the absorbance value (optical density, OD) at 570 nm of each group was determined by the MTT assay.

Steps of the above cultivation and MTT assay were repeated four times. The absorbance values were averaged in each group, and the result of the control group was served as a basis for calculating the relative survival rate of other groups. The results are shown in Table 1 and FIG. 1.

TABLE 1

|  | Concentration of the compound of formula (I) (mg/ml) | | | |
| --- | --- | --- | --- | --- |
|  | 0 | 1 | 0.5 | 0.25 |
| Average of absorbance values (n = 4) | 0.7825 | 0.09575 | 0.17325 | 0.733 |
| Standard deviation | 0.027982 | 0.00818 | 0.040011 | 0.231582 |
| Coefficient of variation | 3.575992 | 8.543353 | 23.09464 | 31.59366 |
| Relative survival rate (%) | 100 | 12.23642 | 22.14058 | 93.67412 |
| Relative standard deviation | 3.575992 | 1.045401 | 5.113285 | 29.59508 |

As shown in Table 1 and FIG. 1, when the final concentration of compound of formula (I) in the medium was higher than 0.25 mg/ml, the survival rate of malignant melanoma cells is inversely proportional to the concentration of the compound of formula (I). These results indicate that compound of formula (I) can effectively induce apoptosis of malignant melanoma cells, and thus, can be used for treating melanoma.

What is claimed is:

1. A method for treating melanoma, comprising administering to a subject in need thereof an effective amount of an active ingredient in a pharmaceutically acceptable form, wherein the active ingredient is selected from the group consisting of a compound of formula (I), a pharmaceutically acceptable salt of the compound of formula (I), and combinations thereof,

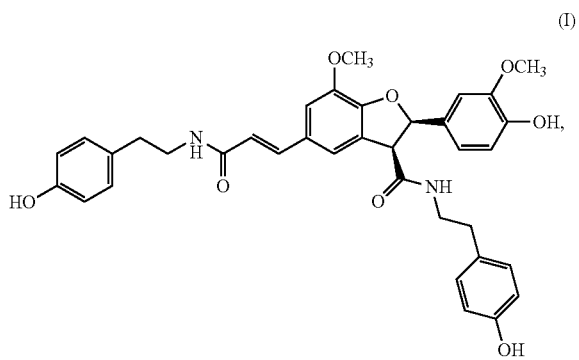 [SMILES: COc1cc([C@@H]2Oc3c(OC)cc(/C=C/C(=O)NCCc4ccc(O)cc4)cc3[C@@H]2C(=O)NCCc2ccc(O)cc2)ccc1O]

(I)

wherein the compound of formula (I) is prepared in the pharmaceutically acceptable form by chemical synthesis or from a plant extract.

2. The method as claimed in claim 1, wherein the active ingredient is used as an extract.

3. The method as claimed in claim 2, wherein the extract is an extract of *Mesembryanthemum crystallinum* L.

4. The method as claimed in claim 2, wherein the extract is a polar solvent extract of *Mesembryanthemum crystallinum* L.

5. The method as claimed in claim 4, wherein the polar solvent is selected from the group consisting of water, C1-C4 alcohols, and combinations thereof.

6. The method as claimed in claim 1, wherein the active ingredient is administered to the subject by at least one of oral administration, percutaneous administration and injection.

7. The method as claimed in claim 6, wherein the active ingredient is administered to the subject by oral administration.

8. The method as claimed in claim 6, wherein the active ingredient is administered to the subject by percutaneous administration.

9. The method as claimed in claim 6, wherein the active ingredient is administered to the subject by injection.

* * * * *